United States Patent
Siegel et al.

(10) Patent No.: US 7,599,057 B2
(45) Date of Patent: Oct. 6, 2009

(54) METHOD AND APPARATUS FOR DETECTION OF BIOLOGICAL ORGANISMS USING RAMAN SCATTERING

(75) Inventors: Neal Arthur Siegel, Morris, IL (US); David R. Fischell, Fair Haven, NJ (US)

(73) Assignee: Sword Diagnostics, Inc., Summit-Argo, IL (US)

( * ) Notice: Subject to any disclaimer, the term of this patent is extended or adjusted under 35 U.S.C. 154(b) by 0 days.

(21) Appl. No.: 11/580,845

(22) Filed: Oct. 16, 2006

(65) Prior Publication Data

US 2007/0087430 A1    Apr. 19, 2007

Related U.S. Application Data

(60) Provisional application No. 60/727,328, filed on Oct. 17, 2005, provisional application No. 60/836,936, filed on Aug. 11, 2006.

(51) Int. Cl.
*G01J 3/44*   (2006.01)
*G01N 21/00*  (2006.01)

(52) U.S. Cl. .................. 356/301; 356/432; 356/929
(58) Field of Classification Search ............... 435/975
See application file for complete search history.

(56) References Cited

U.S. PATENT DOCUMENTS

2003/0059820 A1   3/2003   Vo-Dinh

FOREIGN PATENT DOCUMENTS

| EP | 0 714 025 A1 | 5/1996 |
|---|---|---|
| EP | 0 725 271 A1 | 8/1996 |
| JP | 2000258346 | 9/2000 |
| WO | WO 2004/007767 A2 | 1/2004 |
| WO | WO 2006/096468 A2 | 9/2006 |
| WO | WO 2006/104695 A2 | 10/2006 |
| WO | WO 2007/011778 A2 | 1/2007 |
| WO | WO 2007/047526 A1 | 4/2007 |
| WO | WO 2008/018933 A2 | 2/2008 |

OTHER PUBLICATIONS

Plastino et al (Biochemistry vol. 38, No. 26, pp. 8204-8216, 1999).*
Dou et al (Anal. Chem. vol. 69, pp. 1492-1495, 1997).*
Sengupta, A., et al., "Bioaerosol Characterization by Surface-Enhanced Raman Spectroscopy (SERS)," 36(5-6) Journal of Aerosol Science; Measurement and Characterization of Bioaerosols, 651-664 (2005).
Xu Shuping et al., "Surface-Enhanced Raman Scattering Studies on Immunoassay," 10(3) Journal of Biomedical Optics, 1-12 (2005).
Grow, A., et al., "New Biochip Technology for Label-Free Detection of Pathogens and Their Toxins," 53(2) Journal of Microbiological Methods, 221-223 (2003).
Mosier-Boss, P.A., et al., "Surface-Enhanced Raman Spectroscopy Substrate Composed of Chemically Modified Gold Colloid Particles Immobilized on Magnetic Microparticles," 77(4) Analytical Chemistry, 1031-1037 (2005).
Driskell, J.D., et al., "Low-Level Detection of Viral Pathogens by a Surface-Enhanced Raman Scattering Based Immunoassay," 77(19) Analytical Chemistry, 6147-6154 (2005).
Mosier-Boss, P.A., "Optical Properties of Surface-Enhanced Raman-Active Capture Matrices," 60(10) Applied Spectroscopy, 1148-1156 (2006).
Partial International Search Report in Application No. PCT/US2009/033750, Jul. 21, 2009.

* cited by examiner

*Primary Examiner*—Mark Navarro
(74) *Attorney, Agent, or Firm*—Finnegan, Henderson, Farabow, Garrett & Dunner, L.L.P.

(57) ABSTRACT

A system for the detection of compounds, including a target biological organism or component from a sample, using one or more reactant that will bind to the biological organism or compound forming a Raman active product, concentrating the Raman active product, and detecting the Raman active product using Raman light scattering.

5 Claims, 8 Drawing Sheets

METHOD AND APPARATUS FOR DETECTION OF BIOLOGICAL ORGANISMS USING RAMAN SCATTERING

The present application, U.S. application Ser. No. 11/580,845, filed Oct. 16, 2006, claims the benefit of U.S. provisional application No. 60/727,328, filed Oct. 17, 2005, and the benefit of U.S. provisional application No. 60/836,936, filed Aug. 11, 2006, all of which are incorporated herein by reference.

The present disclosure generally relates to the field of biological diagnostic equipment and testing methods.

There are currently many areas needing systems for the detection of biological organisms or components (e.g. proteins, DNA, or other genetic material). These areas include: food safety, medical diagnostics, veterinary diagnostics, pathogen detection and homeland security. Current methods include immunochemistry, molecular biology or biological techniques such as Polymerase Chain Reaction (PCR) and Ligase Chain Reactions (LCR). These methods and techniques are often limited in accuracy, specificity and sensitivity.

For example, medical diagnostics use immunochemical techniques to provide specificity in the detection of biologically active components of a sample. Antibodies developed to specific compounds are known to have high affinity for these components. In and of themselves antibodies provide limited detectability and as such are typically chemically modified with labels or tags that serve to enhance detection of the antibody during a reaction with the target biological component. In this way, prior art techniques can identify a biologic component. Unfortunately, the ability to detect the antibody is prone to interference from other things in the sample including the sample matrix, wash components and other chemical agents. In addition, current detection techniques lack sensitivity at low concentrations or numbers of antibodies (i.e. low concentrations or numbers of targeted biological components).

Raman light scattering techniques (Raman Spectroscopy) have been used in the past to detect specific chemical components. Raman scattering is a basic property of the interaction of light with molecules. When light hits a molecule it can cause the atoms of the molecule to vibrate. This vibration will then change the energy of additional light hitting the molecule. This additional scattered light has characteristics that are measurable and are unique to the structure of the molecule that was caused to vibrate. Raman spectroscopy by itself lacks specificity and sensitivity for the detection of biological organisms and components.

The present disclosure is directed to methods and apparatus that uses the combination of Raman spectroscopy and biological labeling techniques to identify and quantify biological organisms and components with higher sensitivity and specificity than prior art techniques. Specifically, the use of present disclosure for detecting antibody/biological component combinations can be performed by use of an immunoassay followed by Raman scattering detection techniques.

The immunoassay for certain embodiments of the present invention involves first having an antibody attached to a solid surface bind to the target biologic. Unbound components of the test sample are then washed away leaving only the bound biologic/antibody combinations. At this point the combined biologic/antibody combination can be detected by Raman scattering of ultraviolet light.

In one embodiment, the current invention uses the combination of Raman spectroscopy and biological labeling techniques to identify and quantify biological components, such as proteins or peptides including any post-translational modifications, in specific conformations or conditions associated with disease: for example, prion proteins.

To increase the sensitivity an additional step is envisioned where one or more new reactants are then introduced and become bound to the biologic/antibody combination. The combination of the new reactant(s) with the biologic/antibody combination can now be detected using Raman scattering of light. Examples of such reactants include, but are not limited to:

1. antibodies labeled with Raman active molecules;
2. enzyme/antibody conjugates combined with additional chemical reactants that react to form Raman active molecules;
3. Raman active reactants that chemically interact with the biologic; and
4. chemical reactants that are converted by the biologic into a Raman active molecule.

It is also envisioned that instead of starting with a biologic/antibody combination as in examples 1 and 2 above that the Raman detection methods can use chemicals that interact with the biologic without the antibody as described in examples 3 and 4 above.

It is also envisioned that specific binding partners for the target biologic other than antibodies may be used, for example, a biological receptor (a protein).

Although the techniques disclosed herein are associated with the detection of biological organisms and component, similar techniques are envisioned for the detection of inorganic components, organic components, contaminants or toxins in a sample. Further enhancement of the disclosed detection techniques involves the choice of reactants that exhibit resonance Raman light scattering. In other words, there are frequencies with more intensity in the scattered light which is specific to the structure of the reactant. The resonance phenomena in certain embodiments of the present invention is solely related to the chemical structure and interaction and not to any solid surface interaction such as found in the technique know as Surface Enhanced Resonant Raman Scattering (SERRS) which is a more complex and less desirable process.

It is also envisioned that embodiments of the present disclosure can be implemented on a micro-fluidic channel (or well) integrated circuit using micro or nano-fabrication technology in which the binding partner is immobilized in one or more micro-fluidic channels in a custom integrated circuitry which would also include the laser(s) and detectors for Raman spectroscopy. Such an implementation could detect single biological components such as pathological bacteria, proteins or genetic material.

Thus an object of the present disclosure is to have a system for the detection of target biological organisms of components that utilizes a combination of chemical interactions including binding with a final step of Raman light scattering.

Another object of the present disclosure is to have a system for the detection of target inorganic or organic components that utilizes a combination of chemical interactions including binding with a final step of Raman light scattering.

Another object of the present disclosure is to combine an immunoassay with detection using Raman light scattering.

Still another object of the present disclosure is to increase sensitivity of detection by the use of chemical reactants that produce resonant Raman light scattering.

Yet another object of the present disclosure is to have an integrated circuit design with micro-fluidic channels or wells which can perform the combination of binding and Raman light scattering measurements.

These and other objects and advantages of the present disclosure will become obvious to a person of ordinary skill in this art upon reading of the detailed description of this invention including the associated drawings.

DETAILED DESCRIPTION OF THE DRAWINGS

Figure 1:
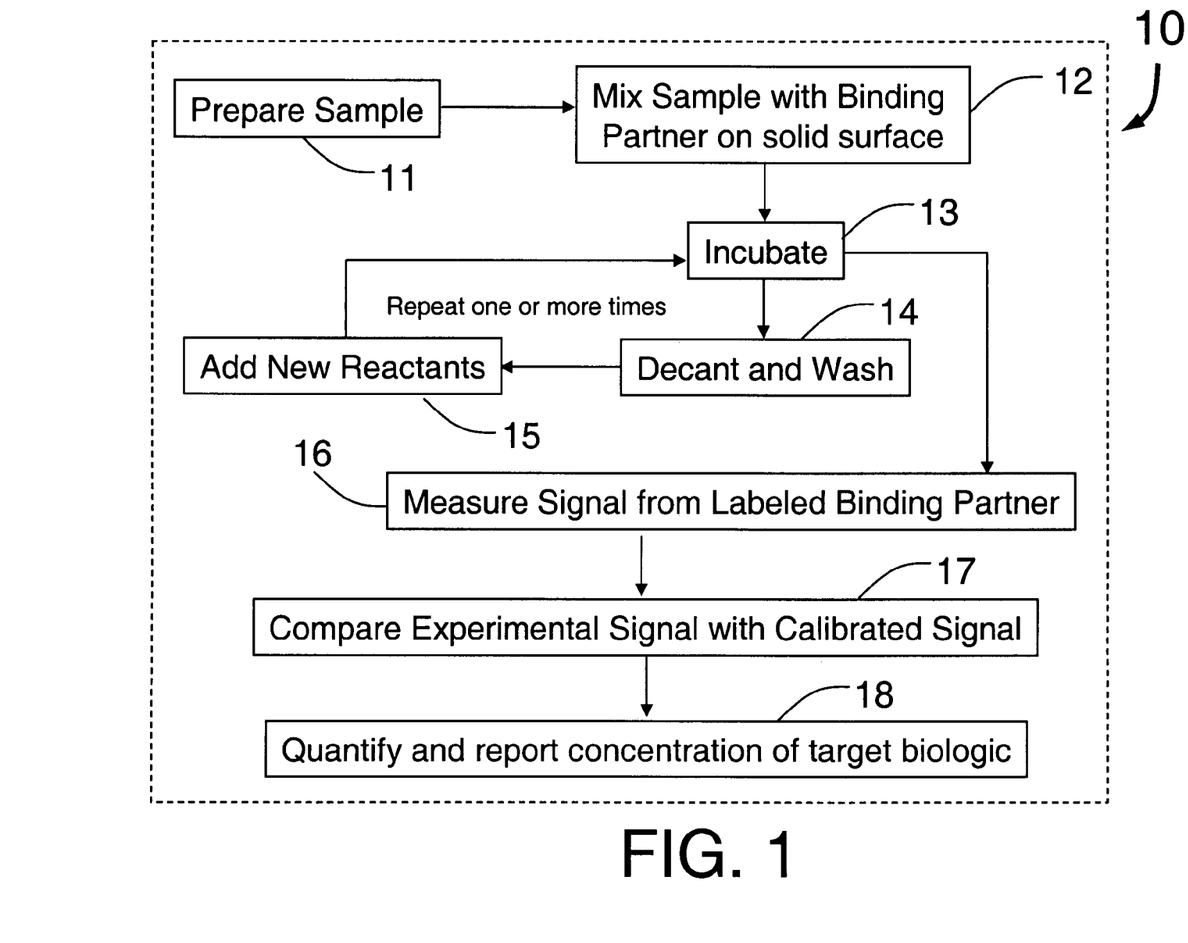
FIG. 1 is a flow chart of a typical prior art immunoassay technique (ELISA) for the detection of biological organisms or components.

FIG. 1 is a flow chart of a typical prior art immunoassay technique (ELISA) 10 for the detection of biological organisms or components. The process begins by the step 11 of preparing the liquid sample that includes the target biologic. For example, the sample can be prepared by pre-enrichment in a growth medium such as half-Frasier's broth or other suitable microbial growth medium. Alternately, a liquid sample for testing may be obtained from any liquid source. Solid material may be immersed in an appropriate liquid solution and potential target organism or molecules placed in solution and then sampled in the liquid. In the next step 12 the prepared liquid sample is combined (or mixed) with a binding partner that has been attached to a solid surface. Typical binding partners include antibodies, bacteriophage, and bacteriophage proteins. For example plastic microtiter plates, latex beads or magnetic microparticles may be used. Other solid supports such as nitrocellulose, filter paper, nylon and other plastics may also be used. The antibody/biologic combination is then incubated in step 13 to allow time for the biologic and antibody to bind together. Once this has occurred the combined binding partner/biologic is decanted (poured off) and washed to remove unbound biologics and other unwanted materials. New reactants are added in step 15 to enhance the sensitivity of the mixture to detection of signal molecules by various methods. Examples of such reactants include:

1. binding partners labeled with radioactive molecules;
2. binding partners labeled with fluorescent molecules;
3. enzyme/binding partner conjugates combined with additional chemical reactants that react to form light absorbing molecules;
4. enzyme/binding partner conjugates combined with additional chemical reactants that react to form light producing molecules; and
5. enzyme/binding partner conjugates combined with additional chemical reactants that react to form light reflecting molecules.

The mixture containing the bound binding partner/biologic and new reactants is the incubated in step 13 to allow time for the reaction to occur. At this point in many cases, the reaction part of the process 10 is complete and step 16 of measuring the molecules produced or included in steps 11 through 15 inclusive can be performed. If additional reactants are required, steps 14, 15 and 13 may be repeated one or more times in succession until the appropriate signal molecules are present.

The measurement of the signal molecule(s) provides a quantitative result that can then be analyzed and compared in step 17 to a known set of calibrated responses of known concentrations of the target biologic. This comparison results in step 18 which is the quantified result and associated report of the concentration of the target biologic in the sample prepared in step 11.

Although the descriptions of the process 10 of FIG. 1 have been associated with the detection of a biological organism or component, the process 10 is also applicable to the detection of many types of molecules to which antibodies or other binding partners can react.

Figure 2:
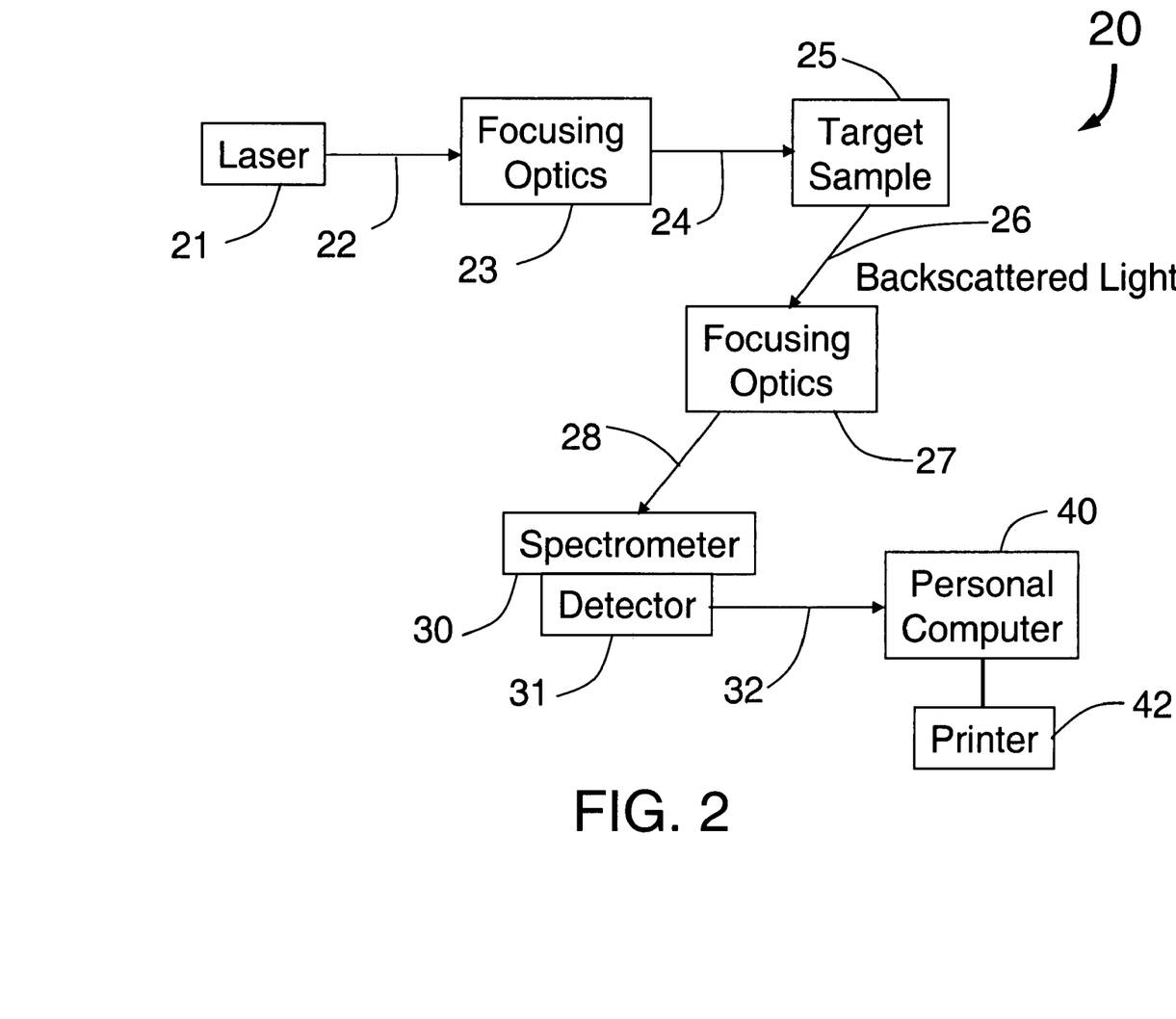
FIG. 2 is a diagram of an embodiment of the disclosed apparatus.

FIG. 2 is a diagram of an embodiment of the present invention detection sub-system 20. A laser 21 produces a laser beam 22 which is focused by the focusing optics 23 into a focused laser beam 24 which hits the target sample 25. The backscattered light 26 from the sample 25 is focused into the beam 28 by the focusing optics 27. The beam 28 is directed into the spectrometer 30 with detector 31. The output from the detector 31 is the signal 32 which is received by the personal computer 40 for analysis, storage and/or printing with the printer 42. The laser 21 is typically a continuous wavelength (CW) laser with output in the visible range. For example, an argon ion laser, helium neon laser, argon ion laser pumped tunable dye laser, or a diode laser in the green, red or other frequency. Focusing optics 23 and 27 include mirrors, lenses, irises, shutters, diffraction gratings, and/or polarizers. The target sample 25 may be liquid, gas or solid and in certain embodiments of the present invention, the target sample would use a liquid or precipitated solid. The spectrometer 30 spatially separates the scattered light based on wavelength. An example of a usable spectrometer for the present invention is the Lambda Solutions model PS-1. The detector 31 measures the amplitude of the light spatially separated by the spectrometer 30 and converts this into an electrical signal (analog or digital). In certain embodiments, the detector would provide the electrical signal using a standardized computer interface such as RS-232, USB, parallel, IEEE 1394. An example of a usable detector 30 for the present invention is a Lambda Solutions PS-1. The personal computer 40 can be any desktop or laptop PC with an appropriate interface to the detector 31 and software designed to analyze, store and/or print the spectrum of the backscattered light 26 received by the spectrometer 30.

Figure 3:
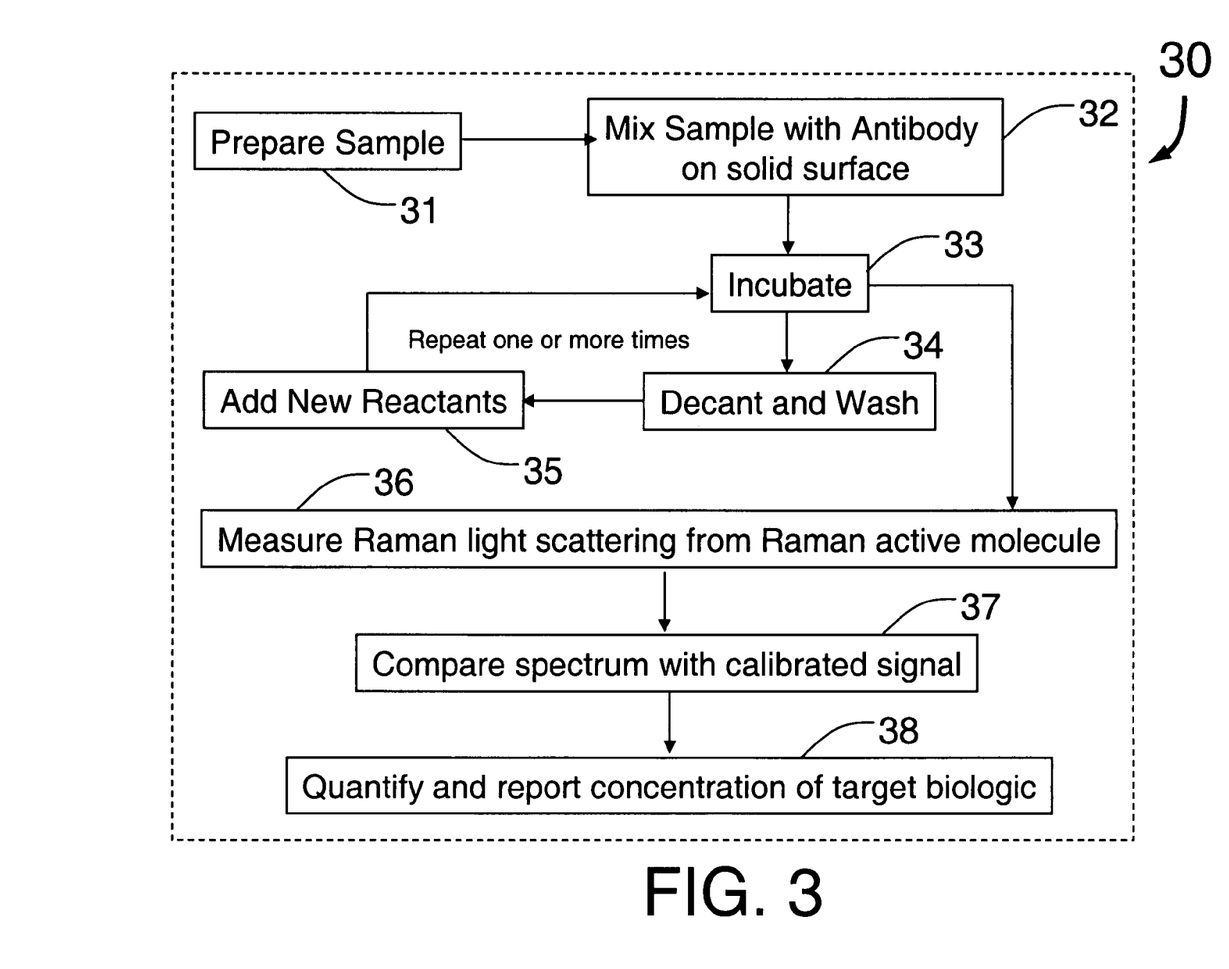
FIG. 3 is a flow chart of an embodiment of the disclosed technique for the detection of biological organisms and/or components.

FIG. 3 is a flow chart of an embodiment of the present invention technique 30 for the detection of biological organisms and/or components. The process begins by the step 31 of preparing the liquid sample that includes the target biologic. For example, the sample may be prepared by pre-enrichment in a growth medium such as half-Frasier's broth or other suitable microbial growth medium. Alternately, a liquid sample for testing may be obtained from any liquid source. Solid material may be immersed in an appropriate liquid solution and potential target organism or molecules placed in solution and then sampled in the liquid. In the next step 32 the prepared liquid sample is combined (or mixed) with an antibody that has been attached to a solid surface. For example, plastic microtiter plates, latex beads or magnetic microparticles may be used. The antibody/biologic combination is then incubated in step 33 to allow time for the biologic and antibody to bind together. Once this has occurred the combined antibody/biologic is decanted (poured off) and washed to remove unbound biologics and other unwanted materials. New reactants are added in step 35 to enhance the sensitivity of the mixture to detection by Raman light scattering. Examples of such reactants include:

1. antibodies labeled with Raman active molecules;
2. enzyme/antibody conjugates combined with additional chemical reactants that react to form Raman active molecules;
3. Raman active reactants that chemically interact with the biologic; and
4. chemical reactants that are converted by the biologic into a Raman active molecule.

The mixture containing the bound antibody/biologic and new reactants is the incubated in step 33 to allow time for the reaction to occur. At this point in many cases, the reaction part of the process 30 is complete and step 36 of measuring Raman light scattering from Raman active molecules produced by steps 31 through 35 inclusive can be performed. If additional reactants are required, steps 34, 35 and 33 may be repeated one or more times in succession until the appropriate Raman active molecules are present.

The measurement of Raman light scattering is a spectrum that can then be analyzed and compared in step 37 to a known set of calibrated responses of known concentrations of the target biologic. This comparison results in step 38 which is the quantified result and associated report of the concentration of the target biologic in the sample prepared in step 31.

For example, Listeria may be measured in an ELISA format. 100 microliters of various concentrations of bacteria; 100,000, 50,000, 25,000, 12,500, 6,250 and 0 colony forming units (cfu) per milliliter are added to microwells coated with anti-Listeria antibodies. After an incubation period between 30 and 60 minutes at 37 C, the wells are decanted and washed with a mild detergent solution three times. 100 microliters of peroxidase-conjugated anti-Listeria antibodies are added to the well and incubated for 1 to 4 hours at 37 C. The wells are decanted and washed with a mild detergent solution three times. A mixture of 4-hydroxyl benzyl alcohol (80.6 mM), 4-aminoantipyrene (24 mM), Urea-Hydrogen Peroxide (10.6 mM) in 125 mM MES buffer (pH 6.0) is added and color is allowed to develop for 30-60 minutes. Raman Spectra of developed color from each well are developed and responses quantified.

Although the descriptions of the process 30 of FIG. 3 have been associated with the detection of a biological organism or component, the process 30 is also applicable to the detection of inorganic or organic molecules, contaminants or toxins.

Figure 4:
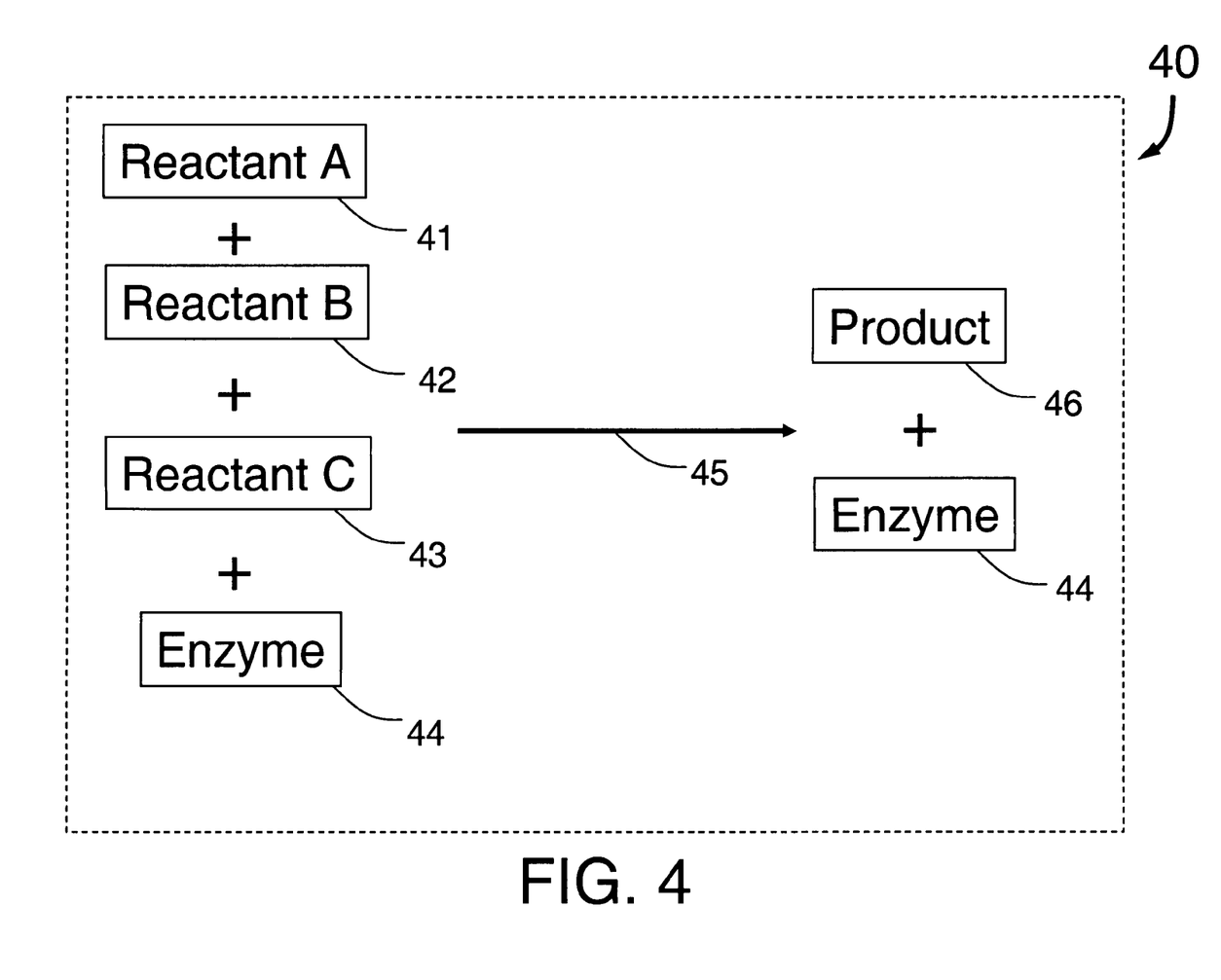
FIG. 4 is a block diagram of the enzyme system for converting chemical components to a Raman active compound.

FIG. 4 is a block diagram for a chemical conversion system 40 which uses an enzyme for converting chemical components to a Raman active compound. For example, one or more reactants designated 41, 42 and 43 are mixed with a biological catalyst 44. The biological catalyst 44 may be an enzyme specific for metabolizing the reactants provided or RNA structures designed to interact with the one or more reactants 41, 42, and 43. A conversion or combination of the reactants occurs in the reaction 45 and a measurable product 46 is formed. For example, the reactants and enzyme shown below are mixed together.

Reactant A, (41) . . . 4-choloro-1-naphthol
Reactant B, (42) . . . 4-aminoantipyrene
Reactant C, (43) . . . Urea Hydrogen peroxide
Enzyme, (44) . . . Horseradish Peroxidase When mixed together, these components will yield an iminoquinone compound which is detectable using Raman spectroscopy or other optical techniques. Reactant 1 may also be phenol, 2-hydroxybenzyl alcohol, 4,5-Dihydroxy-naphthalene-2,7-disulfonic acid or other similar compounds. Reactant 3 may be other electron donating compounds, most notably hydrogen peroxide.

The product of the reaction 45 may be used as a quantitative or qualitative reporting molecule for the reaction and as such may be used as a probe for the presence of specific biological targets if conjoined with, for example, specific antibodies or biological or chemical binding partners.

Figure 5:
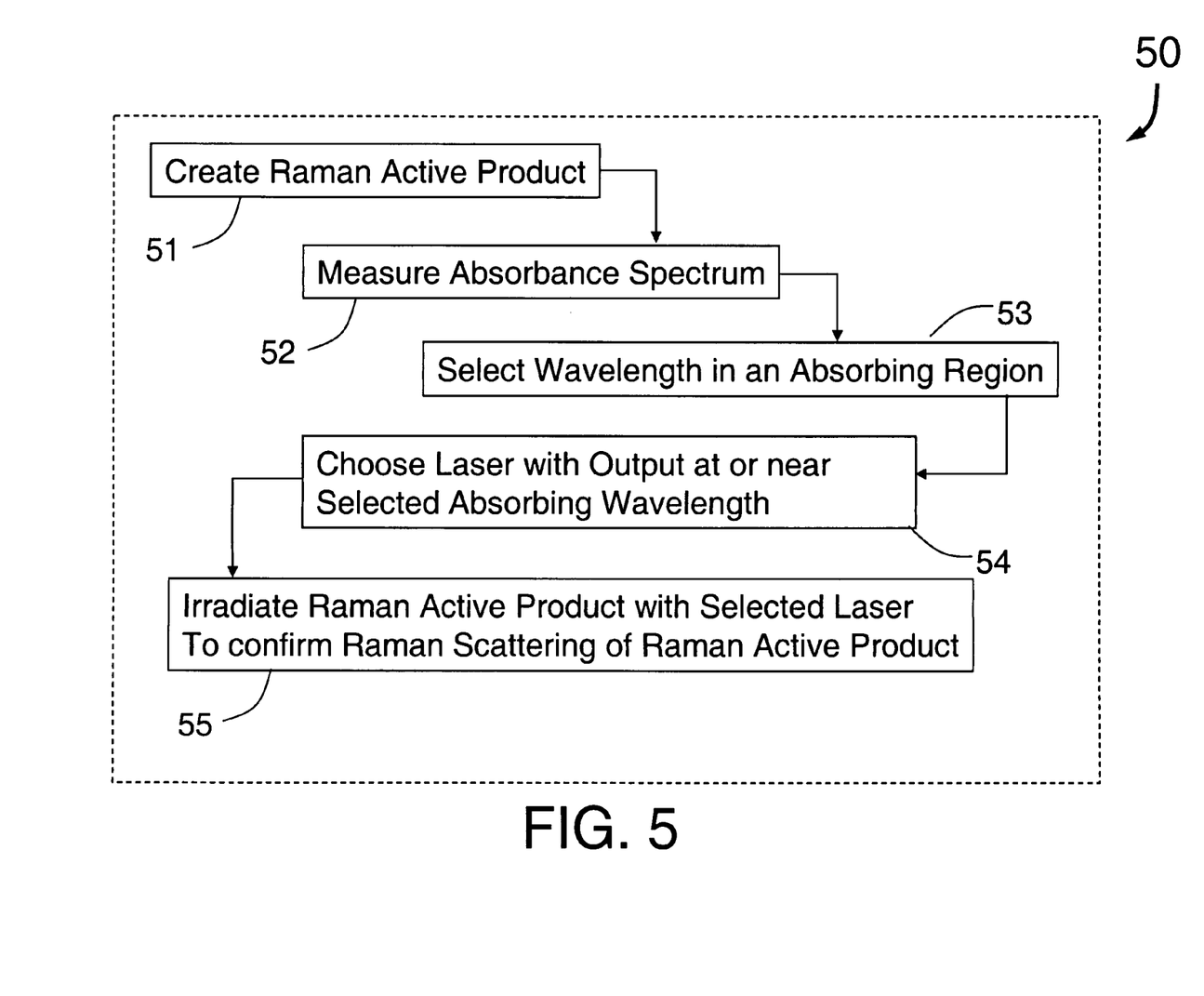
FIG. 5 is a flow chart of a technique for choosing laser light frequencies to excite specific target molecules.

FIG. 5 is a flow chart of the technique 50, for choosing on or more laser light frequencies to excite specific target molecules for resonance Raman detection. A Raman active product 51, such as the product 46 produced by the reaction 45 of FIG. 4, is a chemical that possesses a structure which is Raman active. The absorbance spectrum of the product 51, is measured in step 52 using a technique such as absorbance or transmittance spectrophotometry. In step 53, one or more wavelengths are identified at which the product 51 absorbs light as seen in the spectrum measured in step 52. In step 54, a laser that emits light at a wavelength corresponding to one of the one or more wavelengths identified in step 53 is then selected. Such laser wavelengths can be in the visible range, ultra-violet range or infra-red range. For example, for the Listeria detection reaction 30 described for FIG. 3, the laser wavelength selected is 532 nm.

Finally in step 55 the laser chosen in step 54 is used to irradiate the Raman active product created in step 51. This will confirm that there is significant Raman scattering of the Raman active product created in step 51 to provide adequate signal for detection.

Figure 6:
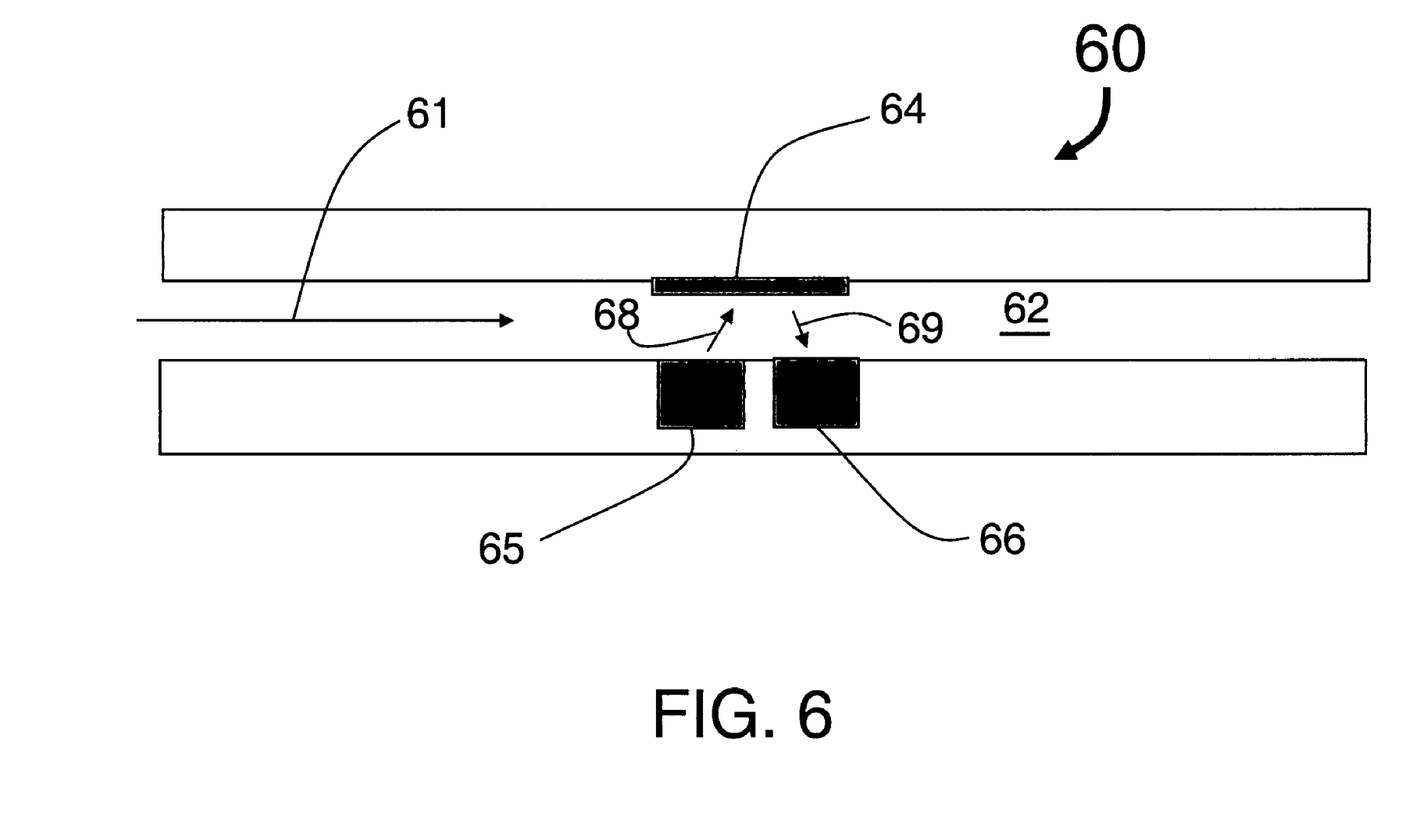
FIG. 6 is an illustration of a micro-fluidic channel designed to detect Raman active compounds.

FIG. 6 is an illustration of a micro-fluidic channel 60 designed to detect Raman active compounds. A source liquid (or gas) sample 61 including the target biological organisms or components flows through the channel 62. The target biological organisms or components will react and be bound to the reactant(s) attached to the active surface 64. Light 68 from the laser 65 produces Raman scattered light 69 which is detected by the photodetector 66. The photodetector is designed to measure one or more specific wavelengths which correspond to the Raman spectrum of the combined reactant(s) and biological organism or component. It is also envisioned that instead of binding the biological organism or component to the surface 64, the reactant(s) may be released from the surface 64 and the Raman scattering laser 65 and detector 66 may be located down stream from the surface 64.

Figure 7:
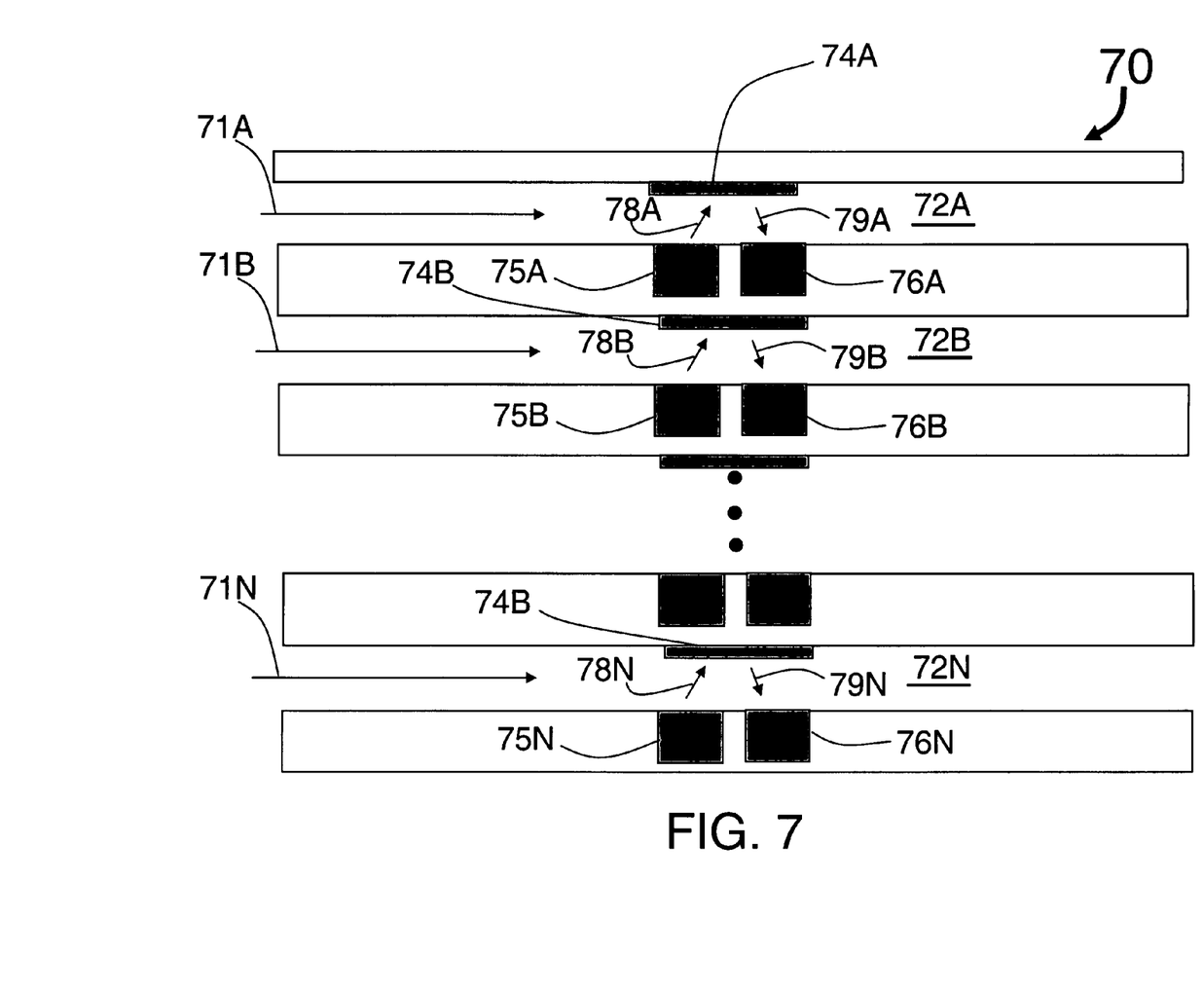
FIG. 7 is an illustration of an array of micro-fluidic channels such as might be incorporated into a custom integrated circuit.

FIG. 7 is an illustration of an array of micro-fluidic channels 70 designed to detect Raman active compounds. One or more source liquid (or gas) samples 71A, 71B through 71N which include the target biological organisms or components flow through the channels 72A, 72B through 72N. The target biological organisms or components will react and be bound to the reactant(s) attached to the active surfaces 74A, 74B through 74N. Light 78A through 78N from the lasers 75 A through 75N produce Raman scattered light 79A through 79N which is detected by the photodetectors 76A through 76N. The photodetectors 76A through 76N are designed to measure one or more specific wavelengths which correspond to the Raman spectrum of the combined reactant(s) and biological organisms or components bound to the surfaces 74A through 74N.

The number of micro-fluidic channels in the array of micro-fluidic channels as limited by the upperbound N, ranges from 2 to 100,000. It is also envisioned that a multiplicity of different reactants and laser wavelengths may be used in different channels. This would allow detection of multiple wavelengths of scattering from the same biological organism or component or it would allow the simultaneous detection of multiple different biological organisms and components. Finally instead of an array of micro-fluidic channels 70, it is envisioned that an array of micro-fluidic wells could be used to produce a 2 dimensional array of Raman scattering detectors.

Figure 8:
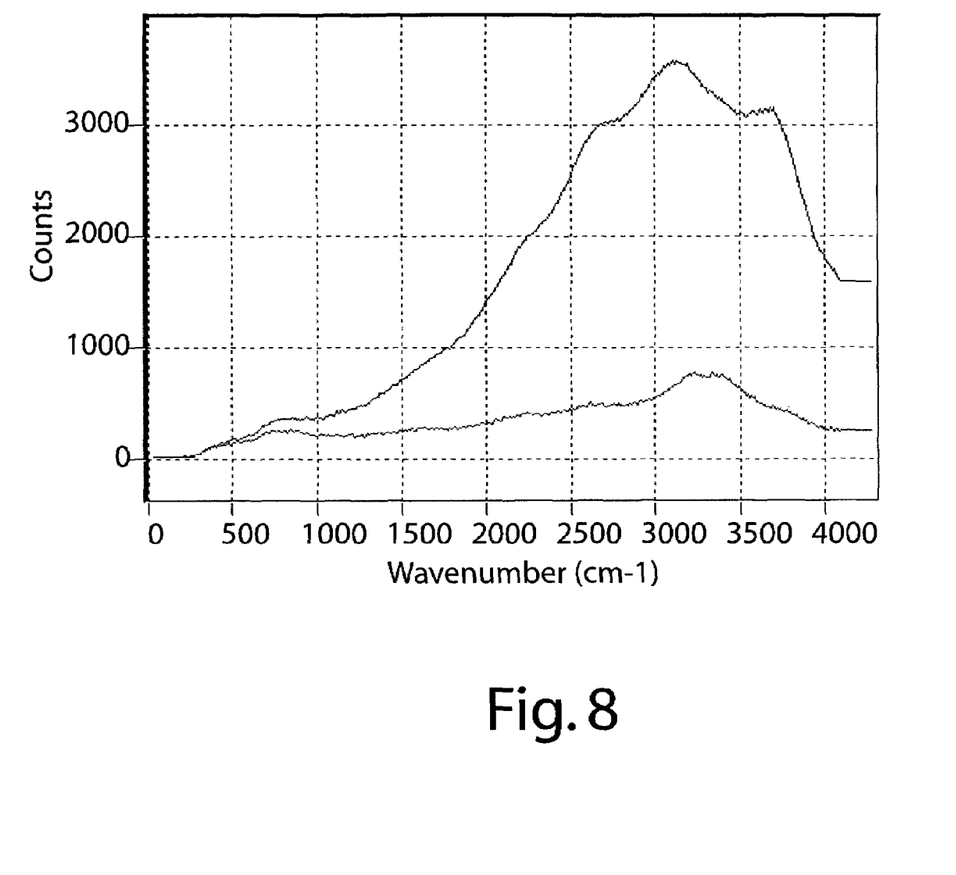
FIG. 8 plots Raman spectra from an enzyme-linked immunoassay for a pathogenic bacteria, *Listeria*, utilizing an antibody linked to peroxidase and with shift numbers (cm-1) plotted on the abscissa and signal magnitudes plotted on the ordinate (arbitrary units) for a sample containing *Listeria* (a) and a sample not containing *Listeria* (b).

FIG. 8 depicts Raman spectra that resulted from an enzyme-linked immunoassay for the pathogenic bacteria *Listeria* utilizing the two-component BASH-UP chemistry, an enzyme-linked antibody, and Raman detection procedure described below utilizing the following reagents.

Working Saline Buffer (used for washes in protocol):
10 mM Sodium Phosphate, pH 6.0
137 mM Sodium Chloride
2.67 mM Potassium Chloride
0.09 mM EDTA
0.05% Bronidox-L
Final Chemistry Reagent (additional to Working Buffer):
0.588 mM 5-Aminosalicylic Acid
0.145 mM 2-Hydroxybenzyl alcohol
0.005 mM L-Ascorbic Acid
1.063 mM Urea Peroxide
0.09% Tween-20
Additional Reagents:
Microparticles-Anti-*Listeria* (antibody) coated magnetic microparticles at 2 million microparticles/sample upon addition
Conjugate Solution-Anti-*Listeria* (antibody) conjugated with Horseradish Peroxidase (HRPO) at 2 uGrams/sample upon addition Samples of either heat-killed *Listeria* or a negative broth (1 ml) were subject to the following procedure. Note, the 1 mL sample may be from culture, control, swab, sponge, etc.

Procedure:
1. Add 100 uliters of microparticles to sample.
2. Incubate 30 minutes at room temperature.
3. Capture microparticles with magnet 10 minutes.
4. Remove sample volume.
5. Add 500 uL Working Saline Buffer, mix 2 minutes at 1000 rpm.
6. Capture microparticles with magnet 2 minutes.
7. Remove wash volume.
8. Repeat steps 3-7 two more times for a total of 3 washes.
9. Add 200 uL Conjugate Solution.
10. Mix solution for 30 minutes.
11. Repeat wash steps 3-7 for a total of 3 washes.
12. Add 200 uL Final Chemistry Reagent.
13. Incubate 20 minutes with mixing at 1000 rpm.
14. Add 40 uL 0.5 N NaOH.
15. Mix 2 minutes at 1000 rpm.
16. Capture microparticles with magnet 2 minutes.
17. Transfer volume to cuvette for Raman signal detection.

In this procedure, the Final Chemistry Reagent was a two component BASH-UP chemistry. Signal was generally stable for ~1 hour or longer. The first component in the chemistry (BASH) contained 2-hydroxy benzyl alcohol (0.02 mg/ml), 5-amino salicylic acid (0.1 mg/ml), 0.1% Tween-20, and ascorbic acid (1 μg/ml) in the Working Saline Buffer (pH 6.0). The second component (UP) contained urea peroxide adduct (1 mg/ml) the working Saline Buffer (pH 6.0) including EDTA (1 mM). These formulations maintained activity when refrigerated out of direct light for more than one month. Mixing the two components at a ratio of 1 UP to 10 BASH created a working solution of BASH-UP that was generally stable for one working day.

An aliquot of the BASH-UP was added to samples containing either heat-killed *Listeria* or a negative broth and allowed to react for 30 minutes. The appropriate period of time will vary based on the sensitivity of detection required. 40 μl of 0.5 N NaOH was added to the 200 μl BASH-UP reaction volume to stop the reaction and render the products Raman detectible. Alteration of the volume and concentration of the NaOH may afford greater signal stability as required by the particular assay.

Raman scattering was observed from the 240 μl sample using a Raman Systems R-3000 Raman spectrometer with a 532 nm laser operated at the high power setting. The results are depicted in FIG. 8.

Embodiments of the current invention include, a system for the detection of a target biological organism or component from a sample comprising one or more reactants that will bind to the biological organism or compound forming a Raman active product; means to concentrate the Raman active product; and a detection sub-system which utilizes Raman light scattering to detect the Raman active product.

Biological organisms that can be detected by embodiments of the present invention include bacteria, viruses. Examples of bacteria that can be detected include *Listeria, E-coli, Salmonella, Staphylococcus, Vibrio* and *Camphelobacter*. Examples of viruses that can be detected by embodiments of the present invention include HIV, Hepatitis, Adenovirus and Rhino virus.

Alternate embodiments of the invention include a system for the detection of *Listeria* from a sample comprising: a means for mixing the sample with a *Listeria* specific antibody bound to a solid surface, the *Listeria* specific antibody being designed to react with and become bound to any *Listeria* present in the sample; a means to incubate the mixed sample and antibody to increase concentration of bound *Listeria*; a means to wash away unwanted material; and a detection sub-system which utilizes Raman light scattering to detect the concentration of bound *Listeria*.

Components that can be detected by embodiments of the present invention include proteins, metabolites, hormones genetic material (e.g. DNA and RNA) and metabolic intermediates.

Various other modifications, adaptations, and alternative designs are of course possible in light of the above teachings. Therefore, it should be understood at this time that, within the scope of the appended claims, the invention can be practiced otherwise than as specifically described herein.

What is claimed is:

1. A system for detecting a biological organism or component in a sample comprising:
   a) one or more reactants that will bind to the biological organism or component, wherein at least one of the one or more reactants comprises one or more enzymes that convert one or more reagents to one or more Raman active products; and
   b) means to separate bound reactants from unbound reactants; and
   c) a detection sub-system which utilizes Raman light scattering to detect the one or more Raman active products, wherein the Raman light scattering is not surface enhanced.

2. The system of claim 1, wherein the one or more enzymes comprise a peroxidase.

3. The system of claim 1, wherein the one or more reagents are chosen from 5-aminosalicyclic acid, 4-aminoantipyrene, 2-hydroxybenzyl alcohol, 4-chloro-1-napththol, phenol, 4,5-dyhydroxynapthalene-2,7 disulfonic acid, L-ascorbic acid, urea hydrogen peroxide, and hydrogen peroxide.

4. The system of claim 2, wherein the one or more reagents comprise 5-aminosalicyclic acid, 2-hydroxybenzyl alcohol, L-ascorbic acid, and urea hydrogen peroxide.

5. The system of claim 4, wherein the one or more reactants comprise an antibody to the target biological organism or component.

* * * * *

UNITED STATES PATENT AND TRADEMARK OFFICE
CERTIFICATE OF CORRECTION

PATENT NO. : 7,599,057 B2
APPLICATION NO. : 11/580845
DATED : October 6, 2009
INVENTOR(S) : Neal A. Siegel et al.

Page 1 of 1

It is certified that error appears in the above-identified patent and that said Letters Patent is hereby corrected as shown below:

In claim 3, column 8, line 57, "4-chloro-1-napththol," should read
--4-chloro-1-naphthol,--.

In claim 3, column 8, lines 57-58, "4,5-dyhydroxynapthalene-2,7 disulfide" should read
--4,5-dihydroxynaphthalene-2,7-disulfide--.

Signed and Sealed this

First Day of December, 2009

David J. Kappos
*Director of the United States Patent and Trademark Office*